United States Patent
Karino

(10) Patent No.: US 10,424,073 B2
(45) Date of Patent: Sep. 24, 2019

(54) IMAGE REGISTRATION DEVICE, METHOD, AND PROGRAM

(71) Applicant: FUJIFILM Corporation, Tokyo (JP)

(72) Inventor: Takatoshi Karino, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 93 days.

(21) Appl. No.: 15/481,939

(22) Filed: Apr. 7, 2017

(65) Prior Publication Data

US 2017/0301100 A1 Oct. 19, 2017

(30) Foreign Application Priority Data

Apr. 13, 2016 (JP) .................................. 2016-079998

(51) Int. Cl.
| | |
|---|---|
| *G06T 7/38* | (2017.01) |
| *A61B 6/00* | (2006.01) |
| *A61B 6/03* | (2006.01) |
| *G06T 7/33* | (2017.01) |
| *G06K 9/00* | (2006.01) |

(52) U.S. Cl.
CPC .............. *G06T 7/38* (2017.01); *A61B 6/032* (2013.01); *A61B 6/481* (2013.01); *A61B 6/486* (2013.01); *A61B 6/503* (2013.01); *A61B 6/507* (2013.01); *A61B 6/5235* (2013.01); *G06K 9/00* (2013.01); *G06T 7/33* (2017.01); *G06T 2200/04* (2013.01);
(Continued)

(58) Field of Classification Search
USPC ....................................................... 382/131
See application file for complete search history.

(56) References Cited

U.S. PATENT DOCUMENTS

2012/0287131 A1 11/2012 Matsuzaki et al.
2012/0323118 A1* 12/2012 Menon Gopalakrishna ................
A61B 6/463
600/431
(Continued)

FOREIGN PATENT DOCUMENTS

| JP | 2009-225943 A | 10/2009 |
|---|---|---|
| JP | 2011-125431 A | 6/2011 |

(Continued)

OTHER PUBLICATIONS

Fieselmann et al., "Deconvolution-Based CT and MR Brain Perfusion Measurement: Theoretical Model Revisited and Practical Implementation Details", International Journal of Biomedical Imaging, vol. 2011, Article ID 467563, 2011, pp. 1-20.
(Continued)

*Primary Examiner* — Justin P. Misleh
(74) *Attorney, Agent, or Firm* — Birch, Stewart, Kolasch & Birch, LLP

(57) ABSTRACT

An image registration device includes: an image acquisition unit that acquires plural images captured in time series; a pixel value change acquisition unit that acquires a pixel value change at the same position of each of the images for plural positions of each image; a clustering unit that clusters the pixel value changes acquired for plural positions of each image into plural classes; a region division unit that divides each of the images into plural regions based on information of the class of each pixel of each image and a pixel value of each pixel of each image; and a registration processing unit that performs registration processing on each image based on information of plural regions of each image.

12 Claims, 3 Drawing Sheets

(52) U.S. Cl.
CPC ............... *G06T 2207/10076* (2013.01); *G06T 2207/10081* (2013.01); *G06T 2207/30048* (2013.01)

(56) References Cited

U.S. PATENT DOCUMENTS

| | | | |
|---|---|---|---|
| 2014/0167569 A1 | 6/2014 | Otera | |
| 2015/0193943 A1* | 7/2015 | Li | G06T 7/0093 382/131 |
| 2015/0335308 A1* | 11/2015 | Pedrizzetti | A61B 8/488 600/454 |
| 2016/0163171 A1* | 6/2016 | Yamazaki | G08B 13/194 348/152 |

FOREIGN PATENT DOCUMENTS

| | | |
|---|---|---|
| JP | 2013-27696 A | 2/2013 |
| JP | 2013-176550 A | 9/2013 |
| JP | 2014-135990 A | 7/2014 |

OTHER PUBLICATIONS

Mani et al., "Survey of Medical Image Registration", Journal of Biomedical Engineering and Technology, vol. 1, No. 2, 2013, pp. 8-25.

Miles, K. A., "Measurement of tissue perfusion by dynamic computed Tomography", The British Journal of Radiology, vol. 64, May 1991, pp. 409-412.

Japanese Notification of Reasons for Refusal for Japanese Application No. 2016-079998, dated Mar. 26, 2019, with English translation.

\* cited by examiner

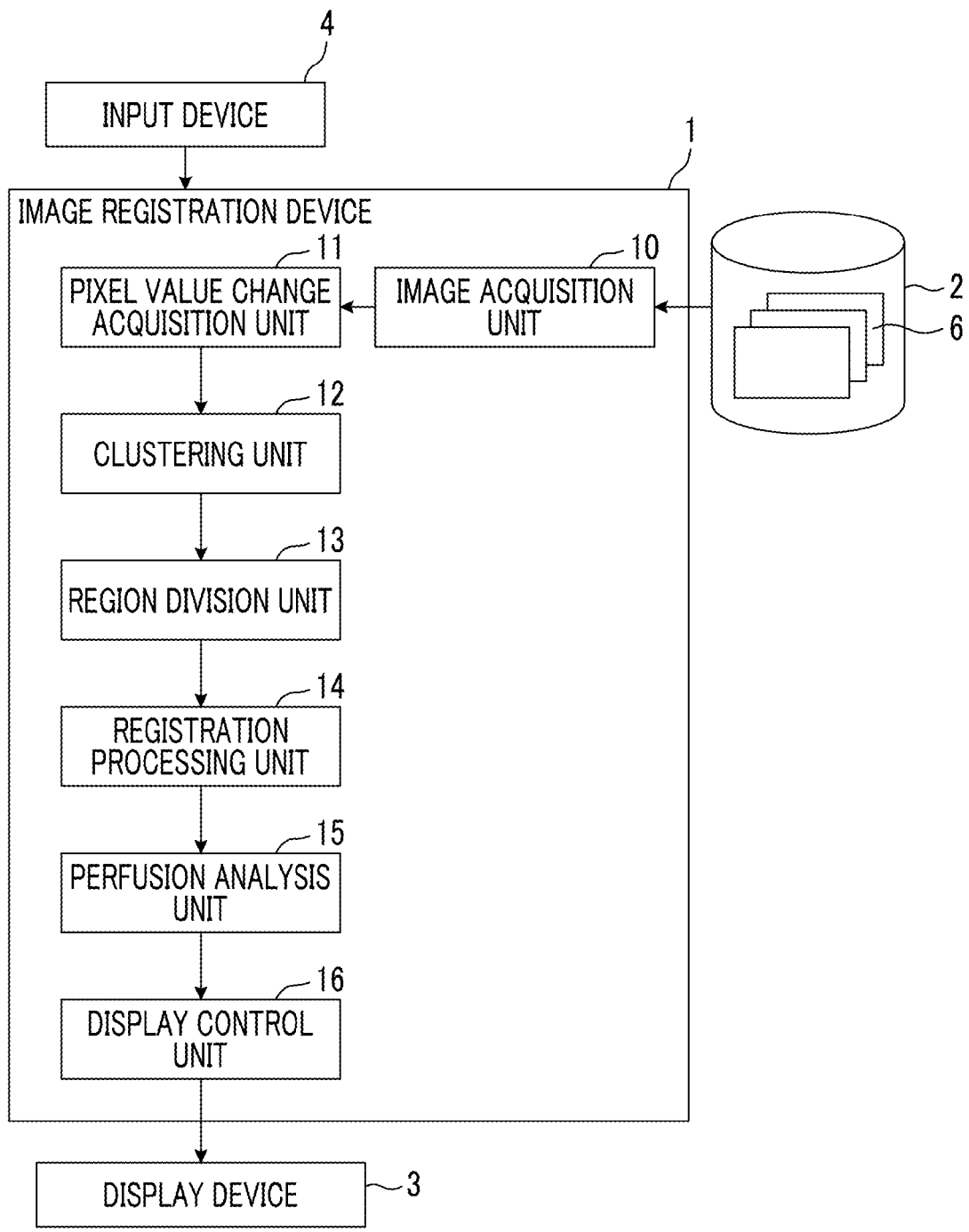

6      IR

IMAGE REGISTRATION DEVICE, METHOD, AND PROGRAM

CROSS-REFERENCE TO RELATED APPLICATIONS

The present application claims priority under 35 U.S.C. § 119 to Japanese Patent Application No. 2016-079998, filed on Apr. 13, 2016. The above application is hereby expressly incorporated by reference, in its entirety, into the present application.

BACKGROUND OF THE INVENTION

1. Field of the Invention

The present invention relates to an image registration device, method, and program for performing registration between a plurality of images.

2. Description of the Related Art

As a known method for measuring the blood flow rate in the myocardium, brain, liver, pancreas, and the like, perfusion imaging has been performed.

Perfusion imaging is an imaging method of injecting a contrast medium into a subject and imaging the subject a plurality of times at different timings using a computed tomography (CT) apparatus or the like. Depending on the phase (imaging timing), images with different anatomical structures contrasted are obtained. Specifically, in the case of the heart, the right atrium and the right ventricle are stained with a contrast medium by injecting the contrast medium through the vein in the initial phase. Then, the contrast medium flows in order of the left ventricle and the left atrium. As a result, the contrast of the cardiac image changes.

An image obtained by perfusion imaging is used for perfusion analysis. The main purpose of perfusion imaging and analysis is to analyze the blood flow of the target organ and diagnose the disease from the result. For example, the blood flow rate obtained by myocardial perfusion analysis is used for diagnosis of myocardial infarction.

As a quantitative analysis method of perfusion (blood flow), there is a maximum slope method (for example, refer to "Measurement of tissue perfusion by dynamic computed tomography.", Miles K A, The British journal of radiology (1991), Vol. 64, No. 761, pp. 409-412) or a deconvolution method (for example, refer to "Deconvolution-based CT and MR brain perfusion measurement: theoretical model revisited and practical implementation details", Fieselmann, Andreas and Kowarschik, Markus and Ganguly, Arundhuti and Hornegger, Joachim and Fahrig, Rebecca, Journal of Biomedical Imaging (2011), Vol. 2011, pp. 14). For these quantitative analyses, a "time density curve (hereinafter, referred to as TDC)" is used. The TDC represents a temporal change in pixel value (CT value) (temporal change in contrast medium concentration) at the position (region) of an organ.

In order to perform highly accurate quantitative analysis, it is necessary to accurately generate a TDC from an image obtained by perfusion imaging. For that purpose, it is necessary to generate a TDC from images of multiple phases by referring to pixel values of the same anatomical position (region). In this case, since it is necessary to accurately match the position of the target organ between phases, image registration is performed.

Registration between images is a problem of finding a geometric transformation T such that a point x of one image $I_F(x)$ (Fixed Image) and a point T(x) of the other image $I_M(x)$ (Moving Image) anatomically match each other. In a case where the geometric transformation T is described using a parameter μ, the registration between images is a problem of finding an optimal solution based on the following Equation (1). The geometric transformation T includes rigid transformation (translation and rotation), Affine transformation, non-rigid transformation (B-Spline and Diffeomorphism), and the like (for example, refer to "Survey of medical image registration", Mani, V R S and others, Journal of Biomedical Engineering and Technology (2013), Vol. 1, No. 2, pp. 8-25).

$$\hat{\mu} = \underset{\mu}{\mathrm{argmin}} S(I_F(\cdot), I_M(T(\cdot\,;\mu))) \qquad (1)$$

S in the above Equation (1) is an evaluation function expressing the degree of matching between the image $I_F(x)$ and the image $I_M(T(\bullet;x))$. In this case, as S decreases, the degree of matching between the two images increases. As evaluation indices of the degree of matching, various evaluation indices, such as a sum of squared difference (SSD: sum of squares of pixel value differences at the same position between two images) or mutual information (one of indicators to quantify the statistical dependence between pixel values), are known.

SUMMARY OF THE INVENTION

Here, in the case of performing registration between images as described above, registration between images in which different anatomical structures are contrasted becomes a problem. For example, in a case where a structure having a high pixel value in one image shows a low pixel value in the other image, pixel values of the same region are different. Accordingly, since the degree of matching is evaluated to be low, it is not possible to perform accurate registration.

As a method of solving such a problem, a method of performing pixel value conversion on the entire image can be considered. Specifically, a method of converting a high pixel value to a low pixel value can be considered.

In the case of this method, however, information regarding the internal structure of an organ to be registered is lost. For example, in the case of myocardial perfusion images, there is a case where only the right atrium and the right ventricle show high pixel values due to the contrast medium in one of two images (refer to FIG. 2A) and not only the right atrium and the right ventricle but also the left atrium and the left ventricle show high pixel values in the other image (refer to FIG. 2B). In such a case, if the same pixel value conversion is applied to the entire image, the above problem can be solved with respect to the left atrium and the left ventricle for which only one image shows high pixel values, which is preferable. However, since the right ventricle and the right atrium show high pixel values in both of the images, shape information that can be used for registration is lost. For this reason, the position inside the organ cannot be adjusted.

JP2011-125431A discloses a technique relevant to registration between images captured by different modalities, such as a CT image and an ultrasound image, but a method of solving the problem described above has not been proposed.

In view of the aforementioned situation, it is an object of the invention to provide an image registration device, method, and program capable of performing registration with high accuracy by reducing the contrast difference between images even in a case where a structure having a high pixel value in one image shows a low pixel value in the other image.

An image registration device of the invention comprises: an image acquisition unit that acquires a plurality of images captured in time series; a pixel value change acquisition unit that acquires a pixel value change at the same position of each of the images for a plurality of positions of each image; a clustering unit that clusters the pixel value changes acquired for a plurality of positions of each image into a plurality of classes; a region division unit that divides each of the images into a plurality of regions based on information of the class of each pixel of each image and a pixel value of each pixel of each image; and a registration processing unit that performs registration processing on each image based on information of a plurality of regions of each image.

In the image registration device of the invention, the image acquisition unit may acquire an image including a cardiac image as an object to be subjected to the registration processing, and the clustering unit may cluster the pixel value changes into at least a class of a myocardium, a class of a right atrium and a right ventricle, and a class of a left atrium and a left ventricle.

In the image registration device of the invention, in a case where a statistical value of a pixel value of the class of the right atrium and the right ventricle is equal to or less than a threshold value set in advance, the region division unit may replace the class of the right atrium and the right ventricle with the class of the myocardium, and divide a region corresponding to the class of the right atrium and the right ventricle and a region corresponding to the class of the myocardium as the same region.

In the image registration device of the invention, in a case where a statistical value of a pixel value of the class of the left atrium and the left ventricle is equal to or less than a threshold value set in advance, the region division unit may replace the class of the left atrium and the left ventricle with the class of the myocardium, and divide a region corresponding to the class of the left atrium and the left ventricle and a region corresponding to the class of the myocardium as the same region.

In the image registration device of the invention, the region division unit may divide each of the images into a plurality of regions by performing graph cut using information of the class of each pixel of each image and a pixel value of each pixel of each image.

In the image registration device of the invention, the registration processing unit may replace a pixel value of each region of each image with a representative value, which is different for each region, based on information of a plurality of regions of each image, and perform the registration processing based on the replaced representative value.

In the image registration device of the invention, in a case where a statistical value of a pixel value of the class of the right atrium and the right ventricle is equal to or less than a threshold value set in advance, the region division unit may replace the class of the right atrium and the right ventricle with the class of the myocardium, and divide a region corresponding to the class of the right atrium and the right ventricle and a region corresponding to the class of the myocardium as the same region. In a case where a region corresponding to the class of the right atrium and the right ventricle in one image to be subjected to registration processing is divided as the same region as a region corresponding to the class of the myocardium and a region corresponding to the class of the right atrium and the right ventricle and a region corresponding to the class of the myocardium in the other image are divided as separate regions, the registration processing unit may replace a pixel value of a region corresponding to the class of the right atrium and the right ventricle in the other image with a representative value of a region corresponding to the class of the myocardium.

In the image registration device of the invention, in a case where a statistical value of a pixel value of the class of the left atrium and the left ventricle is equal to or less than a threshold value set in advance, the region division unit may replace the class of the left atrium and the left ventricle with the class of the myocardium, and divide a region corresponding to the class of the left atrium and the left ventricle and a region corresponding to the class of the myocardium as the same region. In a case where a region corresponding to the class of the left atrium and the left ventricle in one image to be subjected to registration processing is divided as the same region as a region corresponding to the class of the myocardium and a region corresponding to the class of the left atrium and the left ventricle and a region corresponding to the class of the myocardium in the other image are divided as separate regions, the registration processing unit may replace a pixel value of a region corresponding to the class of the left atrium and the left ventricle in the other image with a representative value of a region corresponding to the class of the myocardium.

In the image registration device of the invention, the clustering unit may perform the clustering based on at least one of a peak value of the pixel value change or a time at which the peak value is obtained.

An image registration method of the invention comprises: acquiring a plurality of images captured in time series; acquiring a pixel value change at the same position of each of the images for a plurality of positions of each image; clustering the pixel value changes acquired for a plurality of positions of each image into a plurality of classes; dividing each of the images into a plurality of regions based on information of the class of each pixel of each image and a pixel value of each pixel of each image; and performing registration processing on each image based on information of a plurality of regions of each image.

An image registration program of the invention causes a computer to function as: an image acquisition unit that acquires a plurality of images captured in time series; a pixel value change acquisition unit that acquires a pixel value change at the same position of each of the images for a plurality of positions of each image; a clustering unit that clusters the pixel value changes acquired for a plurality of positions of each image into a plurality of classes; a region division unit that divides each of the images into a plurality of regions based on information of the class of each pixel of each image and a pixel value of each pixel of each image; and a registration processing unit that performs registration processing on each image based on information of a plurality of regions of each image.

According to the image registration device, method, and program of the invention, a plurality of images captured in time series are acquired, and a change in pixel value at the same position of each image is acquired for a plurality of positions of each image. Then, pixel value changes acquired for a plurality of positions of each image are clustered into a plurality of classes, each image is divided into a plurality of regions based on the information of the class of each pixel of each image and the pixel value of each pixel of each image, and registration processing is performed on each image based on the information of a plurality of regions of each image.

As described above, by dividing each image into a plurality of regions using the result of clustering the change in pixel value of each pixel in each image and performing registration processing using the information of the divided regions, it is possible to reduce the contrast difference even in a case where a structure having a high pixel value in one image shows a low pixel value in the other image. As a result, it is possible to perform registration with high accuracy.

BRIEF DESCRIPTION OF THE DRAWINGS

FIG. 1 is a block diagram showing the schematic configuration of a medical image diagnosis assistance system using an embodiment of an image registration device of the invention.

DESCRIPTION OF THE PREFERRED EMBODIMENTS

Figure 2A:
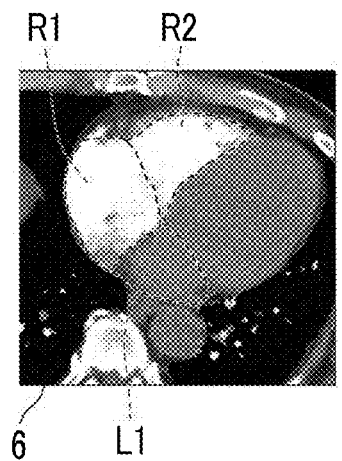
FIGS. 2A to 2C are diagrams showing examples of images obtained by perfusion imaging of the heart.

Hereinafter, a medical image diagnosis assistance system using an embodiment of an image registration device, method, and program of the invention will be described in detail with reference to the diagrams. FIG. 1 is a block diagram showing the schematic configuration of a medical image diagnosis assistance system of the present embodiment.

The medical image diagnosis assistance system of the present embodiment acquires two or more images by imaging the heart or the like in time series, performs registration between these images, and then performs perfusion analysis using the two or more images.

Specifically, as shown in FIG. 1, the medical image diagnosis assistance system of the present embodiment includes an image registration device 1, a medical image storage server 2, a display device 3, and an input device 4.

The image registration device 1 is formed by installing an image registration program of the present embodiment in a computer.

The image registration device 1 includes a central processing unit (CPU), a semiconductor memory, and a storage device such as a hard disk or a solid state drive (SSD). The image registration program of the present embodiment is installed in the storage device. When the image registration program is executed by the central processing unit, an image acquisition unit 10, a pixel value change acquisition unit 11, a clustering unit 12, a region division unit 13, a registration processing unit 14, a perfusion analysis unit 15, and a display control unit 16 that are shown in FIG. 1 operate.

The image registration program is distributed by being recorded on a recording medium, such as a digital versatile disc (DVD) and a compact disc read only memory (CD-ROM), and is installed into the computer from the recording medium. Alternatively, the image registration program is stored in a storage device of a server computer connected to the network or in a network storage so as to be accessible from the outside, and is downloaded and installed into the computer in response to a request.

The image acquisition unit 10 acquires a three-dimensional image 6 captured in advance. The three-dimensional image 6 is obtained by imaging a patient using a CT apparatus or a magnetic resonance imaging (MRI) apparatus, for example. The image acquisition unit 10 of the present embodiment acquires the three-dimensional image 6 captured by so-called perfusion imaging, and acquires cardiac images of two or more phases by imaging the heart, into which a contrast medium is injected, in time series.

Figure 2B:
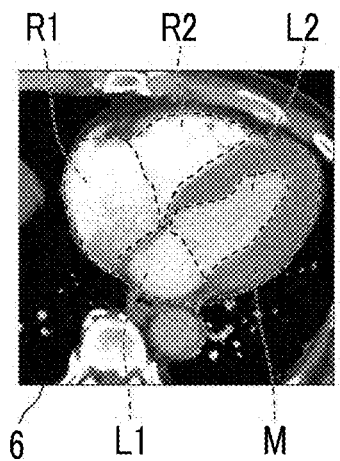
Figure 2C:
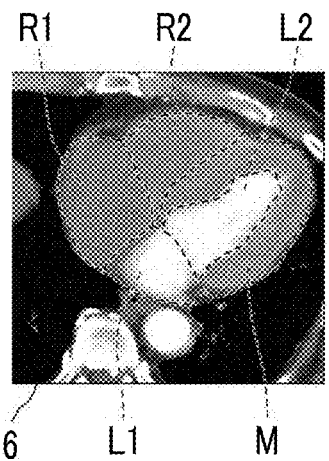

More specifically, the image acquisition unit 10 acquires cardiac images as the three-dimensional image 6 by performing imaging 30 times with one to several heart beats as an imaging interval. It is preferable that the cardiac images of 30 phases are captured in the systole of each heart beat. There is no large difference in the shape of the heart contained in each cardiac image captured in the systole of each heart beat, but there is a deviation of about 1 cm. The deviation of about 1 cm is adjusted by registration processing, which will be described later. FIGS. 2A to 2C are diagrams showing examples of cardiac images of three phases among cardiac images of 30 phases. In the present embodiment, a systolic cardiac image is acquired. However, the invention is not limited thereto, and cardiac images of other phases may be acquired as long as these are cardiac images acquired at timings at which the shapes of the heart almost match each other.

In the present embodiment, the three-dimensional image 6 is acquired by imaging the heart into which a contrast medium is injected. However, the object to be imaged is not limited to the heart, and an image obtained by imaging the liver, the pancreas, the brain, or the like into which a contrast medium is injected may be acquired as the three-dimensional image 6.

As the three-dimensional image 6, volume data configured to include tomographic images, such as axial tomographic images, sagittal tomographic images, and coronal tomographic images, may be acquired, or a single tomographic image may be acquired. Without being limited to the three-dimensional image, two-dimensional images captured in time series by motion picture imaging may be acquired.

The three-dimensional image 6 is stored in the medical image storage server 2 in advance together with the identification information of the patient, and the image acquisition unit 10 reads the three-dimensional image 6 having the identification information from the medical image storage server 2 based on the identification information of the patient, which has been input by the user using the input device 4 or the like, and temporarily stores the read three-dimensional image 6.

Figure 3:
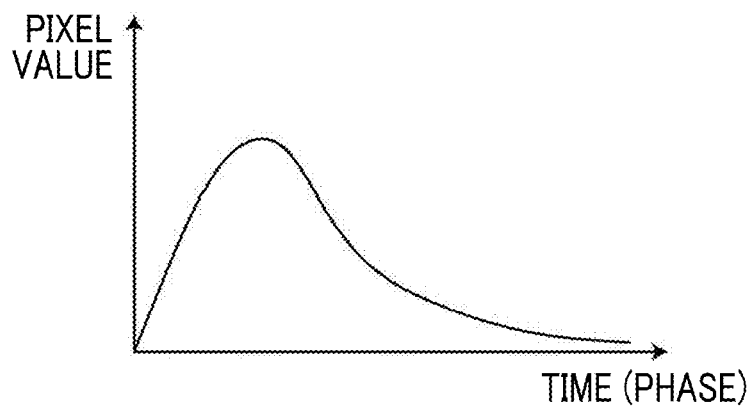
FIG. 3 is a schematic diagram showing an example of a change in pixel value at the same position of a plurality of three-dimensional images.

The pixel value change acquisition unit 11 acquires a change in pixel value at the same position for the three-dimensional image 6 of 30 phases acquired by the image acquisition unit 10. Specifically, a temporal change in pixel value shown in FIG. 3 is acquired. The temporal change in pixel value is acquired as a 30-dimensional vector. It is preferable that the temporal change in pixel value is acquired for all pixel positions of the three-dimensional image. However, the temporal change in pixel value does not necessarily need to be acquired for all pixel positions, and may be acquired for some pixel positions in the three-dimensional image. The number of some pixel positions may be a number sufficient for clustering of pixel values to be described later. In addition, the temporal change in pixel value may be set in advance for some pixel positions, or the user may designate some pixel positions described above on the three-dimensional image 6, which is displayed on the display device 3, using the input device 4.

Figure 4:
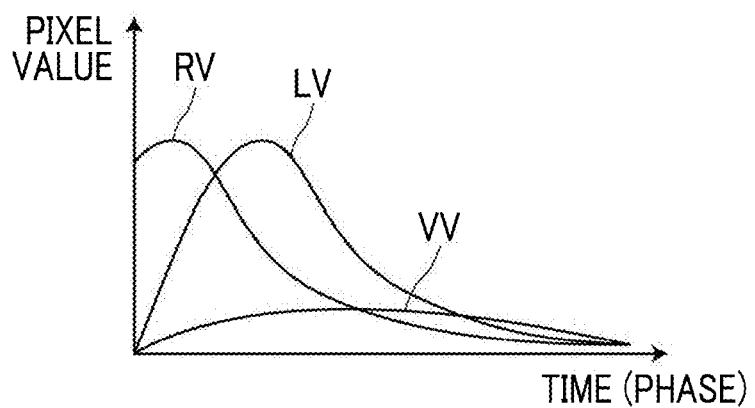
FIG. 4 is a schematic diagram showing examples of a pixel value change RV in the regions of the right atrium and the right ventricle, a pixel value change LV in the regions of the left atrium and the left ventricle, and a pixel value change VV in the region of the myocardium.

The clustering unit 12 clusters pixel value changes at respective pixel positions acquired by the pixel value change acquisition unit 11 into a plurality of classes. For example, in a case where the three-dimensional image 6 is an axial tomographic image of the heart as shown in FIGS. 2A to 2C, pixel value changes acquired by the pixel value change acquisition unit 11 are roughly classified into a pixel value change RV in regions of the right atrium and the right ventricle, a pixel value change LV in regions of the left atrium and the left ventricle, and a pixel value change VV in the region of myocardium as shown in FIG. 4. In FIGS. 2A to 2C, a region R1 is the region of the right atrium, a region R2 is the region of the right ventricle, a region L1 is the region of the left atrium, a region L2 is the region of the left ventricle, and a region M is the region of the myocardium. In FIG. 2A, since the boundary between the left ventricle and the myocardium is not clear, the boundary between these regions is not shown.

The clustering unit 12 clusters pixel value changes at respective pixel positions into the class of the region of the myocardium, the class of the regions of the right atrium and the right ventricle, the class of the regions of the left atrium and the left ventricle, and the class of the other regions. The clustering unit 12 performs clustering using the peak value of the pixel value change at each pixel position and the time at which the peak value is obtained. Specifically, clustering is performed using a k-means method using the Mahalanobis distance. The clustering method is not limited to the k-means method, and other known clustering methods can be used.

In the case of acquiring pixel value changes at some pixel positions without acquiring pixel value changes at all pixel positions of each three-dimensional image, it is preferable to assign class information to pixels other than some pixel positions described above using the clustering result of the pixel value changes.

The region division unit 13 divides each three-dimensional image 6 into a plurality of regions based on the information of the class of each pixel of each three-dimensional image 6 and the pixel value of each pixel of each three-dimensional image 6. Specifically, the region division unit 13 of the present embodiment divides each three-dimensional image 6 into the regions of the right atrium and the right ventricle, the regions of the left atrium and the left ventricle, and the region of the myocardium. As a region division method, for example, a graph cut method can be used.

In the case of using the graph cut method, for example, in the case of dividing each three-dimensional image 6 into the regions of the right atrium and the right ventricle and the other regions, nodes S and T are set in the regions of the right atrium and the right ventricle and the other regions, an n-link connecting adjacent pixels is set based on a difference in pixel value between adjacent pixels, and a t-link connecting each pixel to the node S or the node T is set based on the class information. This is the same for a case of dividing each three-dimensional image 6 into the regions of the left atrium and the left ventricle and the other regions and a case of dividing each three-dimensional image 6 into the region of the myocardium and the other regions. In addition, the regions of the right atrium and the right ventricle, the regions of the left atrium and the left ventricle, and the region of the myocardium may be simultaneously extracted using a multi-class graph cut method.

Here, there is a case where the boundary between the regions of the left atrium and the left ventricle and the region of the myocardium is not clear, for example, as in the three-dimensional image 6 shown in FIG. 2A. In such a case, in the case of performing region division using the graph cut method, highly accurate region division may not be able to be performed in some cases. Therefore, for example, the region division unit 13 of the present embodiment calculates an average pixel value within a region classified into the class of the left atrium and the left ventricle. In a case where the average pixel value is equal to or less than a threshold value (for example, 100) set in advance, the information of the class of the left atrium and the left ventricle is replaced with information of the class of the myocardium, and regions corresponding to the class of the left atrium and the left ventricle and a region corresponding to the class of the myocardium are divided as regions of the same myocardium. Similarly, in the regions of the right atrium and the right ventricle, the region division unit 13 of the present embodiment calculates an average pixel value within a region classified into the class of the right atrium and the right ventricle. In a case where the average pixel value is equal to or less than a threshold value (for example, 100) set in advance, the information of the class of the right atrium and the right ventricle is replaced with information of the class of the myocardium, and regions corresponding to the class of the right atrium and the right ventricle and a region corresponding to the class of the myocardium are divided as regions of the same myocardium.

In the case of the region division described above, the structure information of the right atrium and the right ventricle or the structure information of the left atrium and the left ventricle is lost. However, compared with a case where the region is erroneously divided by the graph cut method, the accuracy of registration processing can be improved.

The registration processing unit 14 performs registration processing on each three-dimensional image 6 based on the information of the region divided by the region division unit 13. Specifically, each pixel value of each three-dimensional image 6 is replaced with a representative value of a constant set in advance for each divided region. For example, in a case where each three-dimensional image 6 is divided into regions of the right atrium and the right ventricle, regions of the left atrium and the left ventricle, and a region of the myocardium, the pixel values of the regions of the right atrium and the right ventricle of each three-dimensional image 6 are replaced with a representative value "0", the pixel values of the regions of the left atrium and the left ventricle are replaced with a representative value "400", the pixel value of the region of the myocardium is replaced with a representative value "700", and the pixel values of the other regions are replaced with a representative value "−100".

Then, registration processing is performed between images whose pixel values have been replaced with constants as described above. As the registration processing, rigid registration processing or non-rigid registration processing is performed. As the rigid registration processing, for example, processing using an iterative closest point (ICP) method can be used. However, other known methods may be used. As the non-rigid registration processing, for example, processing using a free-form deformation (FFD) method or processing using a thin-plate spline (TPS) method can be used. However, other known methods may be used. In addition, after performing the rigid registration processing, the non-rigid registration processing may be performed.

Then, by deforming the three-dimensional image 6 by applying a deformation vector calculated at the time of registration processing between the images whose pixel values have been replaced with constants to the three-dimensional image 6 before replacing the pixel values, the three-dimensional image 6 after the registration processing is generated.

In a case where the boundary between the right atrium and the right ventricle and the myocardium is not clear as described above in one image, on which registration processing is to be performed, and the region division unit 13 divides the regions of the right atrium and the right ventricle and the region of the myocardium as the same region and divides the regions of the right atrium and the right ventricle and the region of the myocardium as separate regions in the other image, the registration processing unit 14 replaces the pixel values of the regions of the right atrium and the right ventricle of the other three-dimensional image 6 with the representative value of the region of the myocardium. In this manner, it is possible to perform registration processing with high accuracy.

In addition, even in a case where the boundary between the left atrium and the left ventricle and the myocardium is not clear in one image, on which registration processing is to be performed, and the region division unit 13 divides the regions of the left atrium and the left ventricle and the region of the myocardium as the same region and divides the regions of the left atrium and the left ventricle and the region of the myocardium as separate regions in the other image, the registration processing unit 14 replaces the pixel values of the regions of the left atrium and the left ventricle of the other three-dimensional image 6 with the representative value of the region of the myocardium.

Figure 5A:
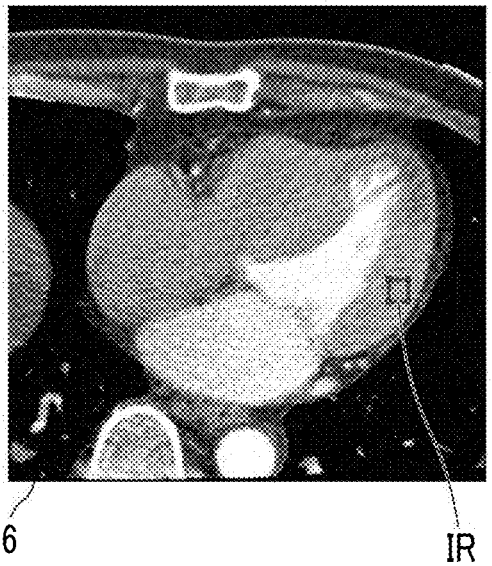
FIGS. 5A and 5B are diagrams illustrating an example of perfusion analysis.
Figure 5B:
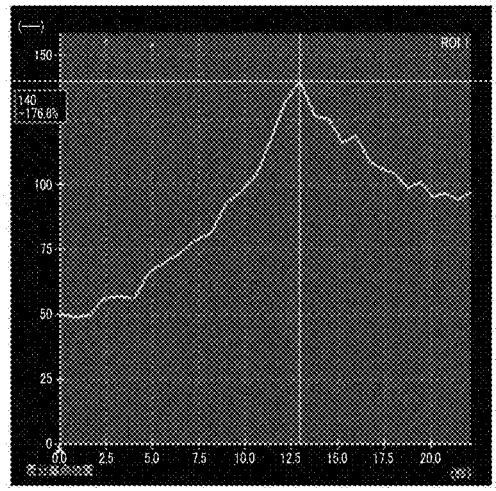

The perfusion analysis unit 15 performs perfusion analysis using the two or more three-dimensional images 6 that have been subjected to registration processing by the registration processing unit 14. As a method of perfusion analysis, the maximum slope method or the deconvolution method described above is used. Specifically, as shown in FIG. 5A, a region of interest IR is designated on the three-dimensional image 6 displayed on the display device 3 by the user. The perfusion analysis unit 15 calculates an average density value of an image in the region of interest IR of each of the two or more three-dimensional images 6 subjected to the registration processing, calculates a time density curve as shown in FIG. 5B, and performs perfusion analysis based on the time density curve.

The display control unit 16 includes a display device, such as a liquid crystal display, and displays the analysis result of the perfusion analysis unit 15 on the display device 3. In addition, the display control unit 16 displays the two or more three-dimensional images 6 acquired by the image acquisition unit 10, the two or more three-dimensional images 6 after registration processing, and the like on the display device 3.

The input device 4 receives various setting inputs from the user, and includes an input device, such as a keyboard or a mouse. For example, the input device 4 receives a setting input of the identification information of a patient, a setting input of the region of interest IR described above, a setting input of a pixel position for acquiring a pixel value change, and the like.

The display device 3 may also be used as the input device 4 by using a touch panel.

Figure 6:
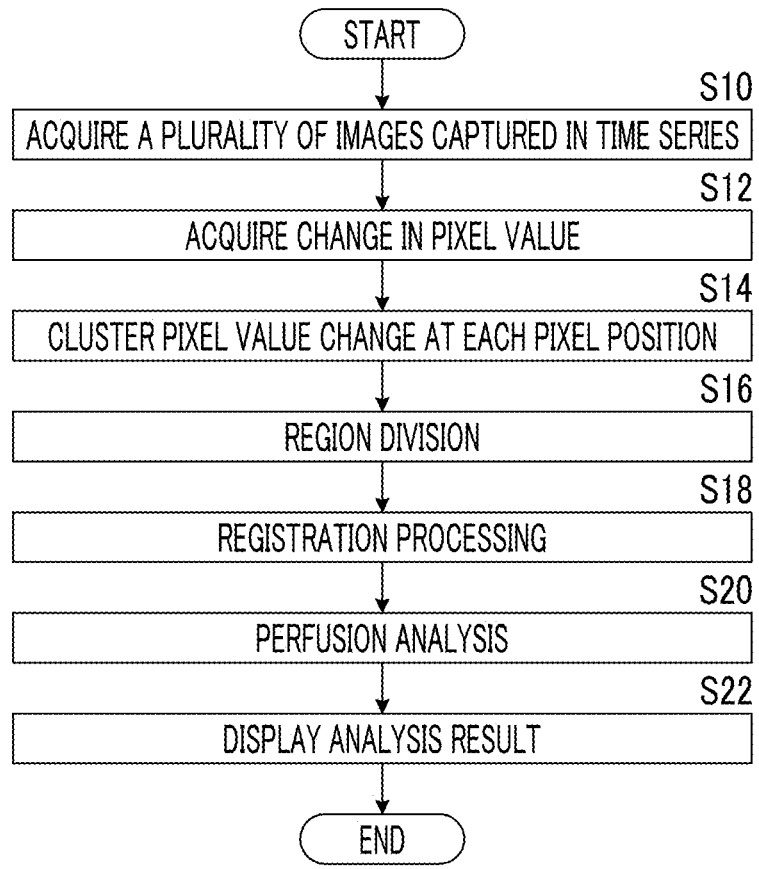
FIG. 6 is a flowchart illustrating the operation of the medical image diagnosis assistance system using an embodiment of the image registration device of the invention.

Next, the operation of the medical image diagnosis assistance system of the present embodiment will be described with reference to the flowchart shown in FIG. 6.

First, based on the input of identification information of a patient from the user, two or more three-dimensional images 6 obtained by perfusion imaging of the patient's heart are acquired by the image acquisition unit 10 (S10).

The two or more three-dimensional images 6 acquired by the image acquisition unit 10 are input to the pixel value change acquisition unit 11. The pixel value change acquisition unit 11 acquires a temporal change in pixel value for each pixel of each three-dimensional image 6 (S12).

Then, the pixel value changes at the respective pixel positions of each three-dimensional image 6 are input to the clustering unit 12, and the clustering unit 12 clusters the pixel value changes at the respective pixel positions into the class of the region of the myocardium, the class of the regions of the right atrium and the right ventricle, the class of the regions of the left atrium and the left ventricle, and the class of the other regions (S14).

Then, the region division unit 13 divides each three-dimensional image 6 into a plurality of regions based on the information of the class of each pixel of each three-dimensional image 6 and the pixel value of each pixel of each three-dimensional image 6 (S16). Specifically, each three-dimensional image 6 is divided into the regions of the right atrium and the right ventricle, the regions of the left atrium and the left ventricle, and the region of the myocardium.

Then, the registration processing unit 14 replaces each pixel value of each three-dimensional image 6 with a representative value set in advance for each divided region, performs registration processing between the images whose pixel values have been replaced with the representative values, and deforms each three-dimensional image 6 using the deformation vector, thereby generating the three-dimensional image 6 after registration processing (S18).

The three-dimensional image 6 subjected to the registration processing is input to the perfusion analysis unit 15, and the perfusion analysis unit 15 performs perfusion analysis using the input three-dimensional image 6 (S20).

The perfusion analysis result of the perfusion analysis unit 15 is input to the display control unit 16, and the display control unit 16 displays the input perfusion analysis result on the display device 3 (S22).

According to the medical image diagnosis assistance system of the embodiment described above, a plurality of images captured in time series are acquired, and a change in pixel value at the same position of each image is acquired for a plurality of positions of each image. Then, pixel value changes acquired for a plurality of positions of each image are clustered into a plurality of classes, each image is divided into a plurality of regions based on the information of the class of each pixel of each image and the pixel value of each pixel of each image, and registration processing is performed on each image based on the information of a plurality of regions of each image.

As described above, by dividing each image into a plurality of regions using the result of clustering the change in pixel value of each pixel in each image and performing registration processing using the information of the divided regions, it is possible to reduce the contrast difference even in a case where a structure having a high pixel value in one image shows a low pixel value in the other image. As a result, it is possible to perform registration with high accuracy.

In the embodiment described above, the registration processing unit 14 replaces the pixel value of each three-dimensional image 6 with a representative value for each region and performs registration processing. However, the method of registration processing is not limited to this method.

For example, the region division unit 13 assigns a label to each region to generate a label image. Specifically, for example, a label image is generated by assigning a label "1" to the regions of the right atrium and the right ventricle of each three-dimensional image 6, assigning a label "2" to the regions of the left atrium and the left ventricle, assigning a label "3" to the region of the myocardium, and assigning a label "4" to the other regions, and the label image is output to the registration processing unit 14 from the region division unit 13.

Then, the registration processing unit 14 calculates the degree of matching using the evaluation function of the following Equation (2).

$$S(L_F(\cdot), L_M(T(\cdot;\mu))) = \frac{1}{N}\sum_{i=1}^{N} C(L_F(x_i), L_M(T(x_i;\mu))) \quad (2)$$

In the above Equation (2), S is an evaluation function of the degree of matching, N is the total number of pixels to be compared between images (between a Fixed image and a Moving image), $x_i$ is a coordinate point, $L_F(x_i)$ is a label at $x_i$ of the Fixed image, $L_M(x_i)$ is a label at $x_i$ of the Moving image, T is a geometric transformation function of the coordinate point, and μ is a parameter of geometric transformation.

The function C in the above Equation (2) is the following Equation (3). The function C outputs a constant K in a case where the labels of $l_1$ and $l_2$ match each other, and outputs 0 (zero) in a case where the labels of $l_1$ and $l_2$ do not match each other. In a case where the function C is defined in this manner, the degree of matching increases as S increases.

$$C(l_1, l_2) = \begin{cases} K & l_1 = l_2 \\ 0 & l_1 \neq l_2 \end{cases} \quad (3)$$

The registration processing unit 14 generates the three-dimensional image 6 after registration processing by calculating the deformation parameter μ to increase the degree of matching S and deforming each three-dimensional image 6 using the deformation parameter μ.

EXPLANATION OF REFERENCES

1: image registration device
2: medical image storage server
3: display device
4: input device
6: three-dimensional image
10: image acquisition unit
11: pixel value change acquisition unit
12: clustering unit
13: region division unit
14: registration processing unit
15: perfusion analysis unit
16: display control unit
IR: region of interest
L1: region of left atrium
L2: region of left ventricle
LV: pixel value changes in regions of left atrium and left ventricle
M: region of myocardium
R1: region of right atrium
R2: region of right ventricle
RV: pixel value changes in regions of right atrium and right ventricle
VV: pixel value change in region of myocardium

What is claimed is:

1. An image registration device, comprising:
a storage device storing an image registration program; and
a central processing unit (CPU) configured to execute the image registration program to:
acquire a plurality of images captured in time series, the plurality of images comprising a first image including a first a plurality of pixels located at first pixel positions in the first image, a second image including a second plurality of pixels located at second pixel positions in the second image, and a third image including a third plurality of pixels located at third pixel positions in the third image, the first pixel positions corresponding to the second pixel positions and to the third pixel positions;
acquire pixel value changes between the first plurality of pixels located at the first pixel positions, the second plurality of pixels located at the second pixel positions, and the third plurality of pixels located at the third pixel positions;
cluster a first pixel value change of the pixel value changes in to a first class, the first pixel value change representing pixels of the first plurality of pixels, pixels of the second plurality of pixels, and pixels of the third plurality of pixels having a same first pixel value change, the first class corresponding to a right atrium of a heart and a right ventricle of the heart;
cluster a second pixel value change of the pixel value changes in to a second class, the second pixel value change representing pixels of the first plurality of pixels, pixels of the second plurality of pixels, and pixels of the third plurality of pixels having a same second pixel value change, the second class corresponding to a left atrium of the heart and a left ventricle of the heart;
cluster a third pixel value change of the pixel value changes in to a third class, the third pixel value change representing pixels of the first plurality of pixels, pixels of the second plurality of pixels, and pixels of the third plurality of pixels having a same third pixel value change, the third class corresponding to a myocardium of the heart;
divide each image of the plurality of images into a plurality of regions corresponding to the first class, the second class, and the third class, the dividing based on the clustering the first pixel value change, the clustering second pixel change, and the clustering the third pixel value change; and
perform registration processing on each image of the plurality of images based on the dividing each image of the plurality of images into the plurality of regions.

2. The image registration device according to claim 1, wherein, in a case where a statistical value of a pixel value associated with the first class is equal to or less than a threshold value set in advance, the CPU replaces pixel values associated with the first class with pixel values associated with the third class, and divides a region corresponding to the first class and a region corresponding to the third class as a same region.

3. The image registration device according to claim 1, wherein, in a case where a statistical value of a pixel value associated with the second class is equal to or less than a threshold value set in advance, the CPU replaces pixel values associated with the second class with pixel values associated with the third class, and divides a region corresponding to the second class and a region corresponding to the third class as a same region.

4. The image registration device according to claim 1, wherein the CPU divides each image of the plurality of images into the plurality of regions by performing graph cut.

5. The image registration device according to claim 1, wherein the CPU replaces a pixel value associated with each region of the plurality of regions with a representative value, the representative value being different for each region, and the performed registration processing is based on the replaced pixel value associated with each region.

6. The image registration device according to claim 1, wherein the CPU performs the clustering based on at least one of a peak value or a time at which the peak value is obtained.

7. An image registration method, comprising:
acquiring a plurality of images captured in time series, the plurality of images comprising a first image including a first a plurality of pixels located at first pixel positions in the first image, a second image including a second plurality of pixels located at second pixel positions in the second image, and a third image including a third plurality of pixels located at third pixel positions in the third image, the first pixel positions corresponding to the second pixel positions and to the third pixel positions;
acquiring pixel value changes between the first plurality of pixels located at the first pixel positions, the second plurality of pixels located at the second pixel positions, and the third plurality of pixels located at the third pixel positions;
clustering a first pixel value change of the pixel value changes in to a first class, the first pixel value change representing pixels of the first plurality of pixels, pixels of the second plurality of pixels, and pixels of the third plurality of pixels having a same first pixel value change, the first class corresponding to a right atrium of a heart and a right ventricle of the heart;
clustering a second pixel value change of the pixel value changes in to a second class, the second pixel value change representing pixels of the first plurality of pixels, pixels of the second plurality of pixels, and pixels of the third plurality of pixels having a same second pixel value change, the second class corresponding to a left atrium of the heart and a left ventricle of the heart;
clustering a third pixel value change of the pixel value changes in to a third class, the third pixel value change representing pixels of the first plurality of pixels, pixels of the second plurality of pixels, and pixels of the third plurality of pixels having a same third pixel value change, the third class corresponding to a myocardium of the heart;
dividing each image of the plurality of images into a plurality of regions corresponding to the first class, the second class, and the third class, the dividing based on the clustering the first pixel value change, the clustering second pixel change, and the clustering the third pixel value change; and
performing registration processing on each image of the plurality of images based on the dividing each image of the plurality of images into the plurality of regions.

8. A non-transitory computer-readable recording medium having stored therein an image registration program causing a computer to:
acquire a plurality of images captured in time series, the plurality of images comprising a first image including a first a plurality of pixels located at first pixel positions in the first image, a second image including a second plurality of pixels located at second pixel positions in the second image, and a third image including a third plurality of pixels located at third pixel positions in the third image, the first pixel positions corresponding to the second pixel positions and to the third pixel positions;
acquire pixel value changes between the first plurality of pixels located at the first pixel positions, the second plurality of pixels located at the second pixel positions, and the third plurality of pixels located at the third pixel positions;
cluster a first pixel value change of the pixel value changes in to a first class, the first pixel value change representing pixels of the first plurality of pixels, pixels of the second plurality of pixels, and pixels of the third plurality of pixels having a same first pixel value change, the first class corresponding to a right atrium of a heart and a right ventricle of the heart;
cluster a second pixel value change of the pixel value changes in to a second class, the second pixel value change representing pixels of the first plurality of pixels, pixels of the second plurality of pixels, and pixels of the third plurality of pixels having a same second pixel value change, the second class corresponding to a left atrium of the heart and a left ventricle of the heart;
cluster a third pixel value change of the pixel value changes in to a third class, the third pixel value change representing pixels of the first plurality of pixels, pixels of the second plurality of pixels, and pixels of the third plurality of pixels having a same third pixel value change, the third class corresponding to a myocardium of the heart;
divide each image of the plurality of images into a plurality of regions corresponding to the first class, the second class, and the third class, the dividing based on the clustering the first pixel value change, the clustering second pixel change, and the clustering the third pixel value change; and
perform registration processing on each image of the plurality of images based on the dividing each image of the plurality of images into the plurality of regions.

9. An image registration device, comprising:
a storage device storing an image registration program; and
a central processing unit (CPU) configured to execute the image registration program to:
acquire a plurality of images captured in time series, the plurality of images comprising a first image including a first a plurality of pixels located at first pixel positions in the first image, a second image including a second plurality of pixels located at second pixel positions in the second image, and a third image including a third plurality of pixels located at third pixel positions in the third image, the first pixel positions corresponding to the second pixel positions and to the third pixel positions; acquire pixel value changes between the first plurality of pixels located at the first pixel positions, the second plurality of pixels located at the second pixel positions, and the third plurality of pixels located at the third pixel positions;

cluster a first pixel value change of the pixel value changes in to a first class, the first pixel value change representing pixels of the first plurality of pixels, pixels of the second plurality of pixels, and pixels of the third plurality of pixels having a same first pixel value change, the first class corresponding to a right atrium of a heart and a right ventricle of the heart;

cluster a second pixel value change of the pixel value changes in to a second class, the second pixel value change representing pixels of the first plurality of pixels, pixels of the second plurality of pixels, and pixels of the third plurality of pixels having a same second pixel value change, the second class corresponding to a left atrium of the heart and a left ventricle of the heart;

cluster a third pixel value change of the pixel value changes in to a third class, the third pixel value change representing pixels of the first plurality of pixels, pixels of the second plurality of pixels, and pixels of the third plurality of pixels having a same third pixel value change, the third class corresponding to a myocardium of the heart;

divide each image of the plurality of images into a plurality of regions corresponding to the first class, the second class, and the third class, the dividing based on the clustering the first pixel value change, the clustering second pixel change, and the clustering the third pixel value change; and perform registration processing on each image of the plurality of images based on the dividing each image of the plurality of images into the plurality of regions, wherein the CPU replaces a pixel value associated with each region of the plurality of regions with a representative value, the representative value being different for each region, and the performed registration processing is based on the replaced pixel value associated with each region, wherein, in a case where a statistical value of a pixel value associated with the first class is equal to or less than a threshold value set in advance, the CPU replaces pixel values associated with the first class with pixel values associated with the third class, and divides a region corresponding to the first class and a region corresponding to the third class as a same region, and in a case where a region corresponding to the first class in one image to be subjected to registration processing is divided as a same region as a region corresponding to the third class and a region corresponding to the first class, and a region corresponding to the third class in another image subjected to registration processing are divided as separate regions, the CPU replaces a pixel value associated with a region corresponding to the first class in the another image with a representative value associated with a region corresponding to the third class.

10. An image registration method, comprising:

acquiring a plurality of images captured in time series, the plurality of images comprising a first image including a first a plurality of pixels located at first pixel positions in the first image, a second image including a second plurality of pixels located at second pixel positions in the second image, and a third image including a third plurality of pixels located at third pixel positions in the third image, the first pixel positions corresponding to the second pixel positions and to the third pixel positions;

acquiring pixel value changes between the first plurality of pixels located at the first pixel positions, the second plurality of pixels located at the second pixel positions, and the third plurality of pixels located at the third pixel positions;

clustering a first pixel value change of the pixel value changes in to a first class, the first pixel value change representing pixels of the first plurality of pixels, pixels of the second plurality of pixels, and pixels of the third plurality of pixels having a same first pixel value change, the first class corresponding to a right atrium of a heart and a right ventricle of the heart;

clustering a second pixel value change of the pixel value changes in to a second class, the second pixel value change representing pixels of the first plurality of pixels, pixels of the second plurality of pixels, and pixels of the third plurality of pixels having a same second pixel value change, the second class corresponding to a left atrium of the heart and a left ventricle of the heart;

clustering a third pixel value change of the pixel value changes in to a third class, the third pixel value change representing pixels of the first plurality of pixels, pixels of the second plurality of pixels, and pixels of the third plurality of pixels having a same third pixel value change, the third class corresponding to a myocardium of the heart;

dividing each image of the plurality of images into a plurality of regions corresponding to the first class, the second class, and the third class, the dividing based on the clustering the first pixel value change, the clustering second pixel change, and the clustering the third pixel value change; and performing registration processing on each image of the plurality of images based on the dividing each image of the plurality of images into the plurality of regions, wherein the CPU replaces a pixel value associated with each region of the plurality of regions with a representative value, the representative value being different for each region, and the performed registration processing is based on the replaced pixel value associated with each region, wherein, in a case where a statistical value of a pixel value associated with the first class is equal to or less than a threshold value set in advance, pixel values associated with the first class are replaced with pixel values associated with the third class, and a region corresponding to the first class and a region corresponding to the third class are divided as the same region, and in a case where a region corresponding to the first class in one image to be subjected to registration processing is divided as a same region as a region corresponding to the third class and a region corresponding to the first class and a region corresponding to the third class in another image subjected to registration processing are divided as separate regions, the pixel value associated with a region corresponding to the first class in the another image subjected to registration processing is replaced with a representative value associated with a region corresponding to the third class.

11. An image registration device, comprising:
a storage device storing an image registration program; and
a central processing unit (CPU) configured to execute the image registration program to:
acquire a plurality of images captured in time series, the plurality of images comprising a first image including a first a plurality of pixels located at first pixel positions in the first image, a second image including a second plurality of pixels located at second pixel positions in the second image, and a third image including a third plurality of pixels located at third pixel positions in the third image, the first pixel positions corresponding to the second pixel positions and to the third pixel positions;
acquire pixel value changes between the first plurality of pixels located at the first pixel positions, the second plurality of pixels located at the second pixel positions, and the third plurality of pixels located at the third pixel positions;
cluster a first pixel value change of the pixel value changes in to a first class, the first pixel value change representing pixels of the first plurality of pixels, pixels of the second plurality of pixels, and pixels of the third plurality of pixels having a same first pixel value change, the first class corresponding to a right atrium of a heart and a right ventricle of the heart;
cluster a second pixel value change of the pixel value changes in to a second class, the second pixel value change representing pixels of the first plurality of pixels, pixels of the second plurality of pixels, and pixels of the third plurality of pixels having a same second pixel value change, the second class corresponding to a left atrium of the heart and a left ventricle of the heart;
cluster a third pixel value change of the pixel value changes in to a third class, the third pixel value change representing pixels of the first plurality of pixels, pixels of the second plurality of pixels, and pixels of the third plurality of pixels having a same third pixel value change, the third class corresponding to a myocardium of the heart;
divide each image of the plurality of images into a plurality of regions corresponding to the first class, the second class, and the third class, the dividing based on the clustering the first pixel value change, the clustering second pixel change, and the clustering the third pixel value change; and
perform registration processing on each image of the plurality of images based on the dividing each image of the plurality of images into the plurality of regions,
wherein the CPU replaces a pixel value associated with each region of the plurality of regions with a representative value, the representative value being different for each region, and the performed registration processing is based on the replaced pixel value associated with each region,
wherein, in a case where a statistical value of a pixel value associated with the second class is equal to or less than a threshold value set in advance, the CPU replaces pixel values associated with the second class with pixel values associated with the third class, and divides a region corresponding to the second class and a region corresponding to the third class as a same region, and
in a case where a region corresponding to the second class in one image to be subjected to registration processing is divided as a same region as a region corresponding to the third class and a region corresponding to the second class and a region corresponding to the third class in another image subjected to registration processing are divided as separate regions, the CPU replaces a pixel value associated with a region corresponding to the second class in the another image with a representative value associated with a region corresponding to the third class.

12. An image registration method, comprising:
acquiring a plurality of images captured in time series, the plurality of images comprising a first image including a first a plurality of pixels located at first pixel positions in the first image, a second image including a second plurality of pixels located at second pixel positions in the second image, and a third image including a third plurality of pixels located at third pixel positions in the third image, the first pixel positions corresponding to the second pixel positions and to the third pixel positions;
acquiring pixel value changes between the first plurality of pixels located at the first pixel positions, the second plurality of pixels located at the second pixel positions, and the third plurality of pixels located at the third pixel positions;
clustering a first pixel value change of the pixel value changes in to a first class, the first pixel value change representing pixels of the first plurality of pixels, pixels of the second plurality of pixels, and pixels of the third plurality of pixels having a same first pixel value change, the first class corresponding to a right atrium of a heart and a right ventricle of the heart;
clustering a second pixel value change of the pixel value changes in to a second class, the second pixel value change representing pixels of the first plurality of pixels, pixels of the second plurality of pixels, and pixels of the third plurality of pixels having a same second pixel value change, the second class corresponding to a left atrium of the heart and a left ventricle of the heart;
clustering a third pixel value change of the pixel value changes in to a third class, the third pixel value change representing pixels of the first plurality of pixels, pixels of the second plurality of pixels, and pixels of the third plurality of pixels having a same third pixel value change, the third class corresponding to a myocardium of the heart;
dividing each image of the plurality of images into a plurality of regions corresponding to the first class, the second class, and the third class, the dividing based on the clustering the first pixel value change, the clustering second pixel change, and the clustering the third pixel value change; and
performing registration processing on each image of the plurality of images based on the dividing each image of the plurality of images into the plurality of regions,
wherein the CPU replaces a pixel value associated with each region of the plurality of regions with a representative value, the representative value being different for each region, and the performed registration processing is based on the replaced pixel value associated with each region,
wherein, in a case where a statistical value of a pixel value associated with the second class is equal to or less than a threshold value set in advance, pixel values associated with the second class are replaced with pixel values associated with the third class, and a region corresponding to the second class and a region corresponding to the third class are divided as the same region, and in a case where a region corresponding to the second class in one image to be subjected to registration processing is divided as a same region as a region corresponding to the third class and a region corresponding to the second class and a region corresponding to the third class in another image subjected to registration processing are divided as separate regions, a pixel value associated with a region corresponding to the second class in the another image is replaced with a representative value associated with a region corresponding to the third class.

* * * * *